US006061141A

United States Patent [19]
Goldenberg et al.

[11] Patent Number: 6,061,141
[45] Date of Patent: May 9, 2000

[54] METHOD AND SYSTEM FOR DETECTING GASES OR VAPORS IN A MONITORED AREA

[75] Inventors: Ephraim Goldenberg; Shaul Serero, both of Rishon Le-Zion; David Cohen, Ashkelon; Yechiel Spector, Zahala; Esther Jacobson, Tel Aviv, all of Israel

[73] Assignee: Spectronix Ltd., Sderut, Israel

[21] Appl. No.: 09/009,421

[22] Filed: Jan. 20, 1998

[51] Int. Cl.$^7$ ................................................. G01N 21/31
[52] U.S. Cl. ............................................. 356/437; 356/411
[58] Field of Search ................................... 356/437, 409, 356/410, 411; 250/343, 345

[56] References Cited

U.S. PATENT DOCUMENTS

| | | | |
|---|---|---|---|
| 3,571,589 | 3/1971 | Barringer . | |
| 3,723,731 | 3/1973 | Blau | 250/437 |
| 3,770,354 | 11/1973 | Tsuruta et al. | 356/407 |
| 4,017,191 | 4/1977 | Bunge | 356/437 |
| 4,193,694 | 3/1980 | Smith | 356/411 |
| 4,567,366 | 1/1986 | Shinohara . | |
| 5,128,797 | 7/1992 | Sachse et al. | 356/414 |
| 5,281,816 | 1/1994 | Jacobson et al. | 250/339 |
| 5,745,243 | 4/1998 | Wilcox et al. | 356/419 |

FOREIGN PATENT DOCUMENTS

95/25950  9/1995  WIPO .

*Primary Examiner*—Richard A. Rosenberger
*Attorney, Agent, or Firm*—Mark M. Friedman

[57] ABSTRACT

A method of detecting the presence of a predetermined vapor of a predetermined concentration in a monitored area, the method including the steps of (a) exposing gas in or from the monitored area to radiation at wavelengths at least covering and surrounding from both sides a main absorption peak of the vapor; (b) simultaneously sensing the radiation after passing through the gas by a signal sensor and a reference sensor, each of the sensors including a radiation sensing element, wherein the signal sensor further includes a first optical filter passing wavelengths covering the main absorption peak, yet substantially blocking wavelengths from both sides of the main absorption peak of the vapor, whereas the reference sensor further includes a second optical filter passing wavelengths surrounding from both sides the main absorption peak, yet substantially blocking wavelengths covering the main absorption peak of the vapor; and (c) comparing signals obtained from the signal and reference sensors for determining a presence or absence of the vapor of the predetermined concentration in the gas.

33 Claims, 3 Drawing Sheets

METHOD AND SYSTEM FOR DETECTING GASES OR VAPORS IN A MONITORED AREA

FIELD AND BACKGROUND OF THE INVENTION

The present invention relates to a method, and also to system, for detecting the presence of predetermined gases or vapours of predetermined concentrations in a monitored area. The invention is particularly useful for detecting hydrocarbon and other gases or vapours when they are present at a concentration which might indicate a possible flammable, explosive or toxic atmosphere.

The increase in the global awareness to the changes in the environment is caused by two major trends observed in the atmosphere, ozone depletion and global warming.

The first alarming change in the atmosphere observed in the late 80's was the hole in the ozone layer and it's continuing depletion caused by various chemicals emitted into the atmosphere, such as chloro-fluoro-carbons (CFC), halocarbons, acids, etc.

The second alarming change in the surrounding atmosphere is the global warming effect caused by the various pollutants released into the atmosphere by industrial processes, creating a "green house" effect whereby infrared radiation from the sun and the Earth is trapped in the atmosphere, causing continuous warming of the environment.

In order to preserve the existing environment, "Clean Air Act" type legislation has been issued World-wide and enhanced the ecological awareness.

In addition to the ecological awareness, the safety of personnel in hazardous environments such as flammable, explosive or toxic atmospheres has also been re-evaluated and criteria for establishing the safety of the environment according to its flammability/explosive or toxic potential have been determined.

Fugitive emissions from various industrial sites have been identified, quantified and permits for allowable concentrations of certain gases have been issued. Lists of flammable, toxic and hazardous gases have been compiled, including their maximum allowable safe concentrations (threshold limit value—TLV, time-weighted average—TWA) and lower limits of explosion or flammability (LEL).

Several areas of environmental awareness can be defined: (i) determination of toxic materials according to "Clean Air Act"; (ii) pollution monitoring (urban and industrial); and (iii) petrochemical unwanted emissions.

In order to facilitate the enforcement of the international legislation and the Clean Air Act, accurate, real time monitoring of various toxic pollutants, CFC, halons (halocarbons), flammable gases, etc., is required.

For facilities operating in today's competitive, highly regulated environment, cost and performance pressures have enforced continuous emission monitoring (CEM) developers towards innovation to improve performance while containing capital and plant operating costs. In-situ to monitoring systems are a cost effective option for applications that require surveillance of a specific component or a chemical family in a gas stream. Novel systems gather measurements either as point concentrations or as an across the area average, using spectral-based analysers.

For process plants that routinely handle toxic or combustible gases, a monitoring system can serve many purposes. For instance adequate monitoring can provide an early warning of a gas leak, which may allow the operators to take the steps needed—either manually or automatically—to reduce the likelihood of fire and explosion, protect personnel, reduce property damage and minimize interruption of production activities. Gas detection systems determine a product release before the resulting vapour is capable of supporting deflagration, detonation or injuring (intoxication) personnel.

To design a monitoring system, the relevant hazards, potential monitoring methods and target location must all be identified. These parameters will vary depending on the facility configuration and type of pollutant under surveillance.

Different monitoring criteria apply to different areas of a process plant. For example in a liquified—gas (LPG) storage area, a gas monitoring system may be needed only to provide an alarm, while in a more populated area of the facility the gas sensing system may be relied upon to initiate process, shut down or actuate air ventilation or water spray systems to dilute the released gas cloud.

In general, more rapid detection of smaller quantities of gas are needed in congested process areas than in open storage areas. For example on offshore platforms the process areas is congested with pipe lines, seals, switches, controllers that pose many potential ignition sources in a rather small area (about 40 m×40 m) and in some cases a flash fire not detected in time may cause extreme damage or construction failure. The Piper Alpha offshore oil platform that was destroyed by a catastrophic fire in July 1988 serves as an example.

The requirement of early warning when a gas is detected at, for example, 20% of it's lower explosive limit (LEL) and alarm when the concentration reaches 40% of LEL is a must in today's industrial environment. Most advanced systems, recently introduced into the market offer early-warning gas detection capabilities combined (in the same system) with early flame detection.

For toxic gas monitoring equipment the requirement to detect traces or very small quantities of gas in the air (at concentrations of parts per million—ppm), in order to meet the OSHA/EPA specifications (for TLV, TWA, STEL or LOAEL and NOAEL toxicological indices) initiated the development of very sensitive systems.

Summarizing briefly the gas detection methods employed today in various monitoring and analytical systems, they can be classified in two main groups point detection and remote optical detection methods.

Point detection methods require gas to be drawn from a monitored area, sampled over a period of time, introduced into a dedicated sample cell of the detection system via a probe/pump/permeable filter and analyzed according to one or several of the following methods: resistance temperature detector (RTD); catalytic-combustion; electro-chemical cells; total organic carbon analysis (TOC); flame ionization detector (FID); gas chromatographic; mass-spectrometry; ion mobility spectrometry (IMS); surface acoustic waveguide (SAW); chemical adsorption, such as surface acoustic waveguide (SAW) and surface optical waveguide (SOW); and optical spectroscopy, e.g., in the ultraviolet (UV), infrared (IR) and visible (VIS) spectral ranges.

Remote (open path) optical detection methods rely on "spectral finger-print" absorption pattern of substance/vapour in air to be determined over the optical line of sight open-path in front of the detector or between a radiation source and a detector.

The remote methods are divided in passive and active methods.

In passive methods a detector is calibrated to detect background radiation (from the sun and earth) and identify the spectral absorption of a gas or vapour against this background. FTIR (Fourier Transform Infrared) spectrometry is a well known technique used in monitoring equipment. Several types of FTIR instruments (for laboratory or field applications) are employed for detection of very low concentrations of gases that have an IR absorption spectra. However, these instruments are quite sensitive to tough/extreme environments, are rather big and cumbersome, and require frequent calibration and highly skilled technical operators, extensive spectra library memory, and most important, are expensive for every day industrial monitoring applications.

The requirement for simple, rugged, explosion proof instruments, that can be used in extreme weather conditions and tough envirorunents, that require very simple installation and servicing practices, that are less expensive and cost effective on installation/weight and area coverage, has initiated the development of a new family of remote gas monitoring instruments based on active detection methods.

In active methods an artificial radiation source and a detector are communicating so that a gas passing the line of sight between them would be detected according to its spectral absorbance. Several active methods have been developed in the recent years, most of them analyzing the spectral absorbance of a gas in several spectral bands thus comparing several signals simultaneously. The following lists some of the active methods employed.

Dual optical absorption spectra (DOAS). This method employs the gas analysis in two adjacent bands (reference band where the gas does not absorb and a gas absorption band).

UV/IR. This method employs several spectral bands in the UV and IR bands, thus comparing the substance spectral finger-print in a wider spectral range. The method can also be employed to detect and differentiate between several gaseous substances to be detected.

IR. This method employs spectral analysis of reference/gas absorption bands in the IR band, preferably the near IR, i.e., 1–5 $\mu$m.

UV. This method employs spectral analysis of reference/gas absorption bands in the UV band, preferably the solar blind 200–300 nm band.

Since each chemical substance has an unique "spectral finger-print" absorption in the UV, VIS, IR portions of the electromagnetic spectrum and the absorption intensity can be related to the concentration of the chemical substance by the Beer-Lambert Law (see below).

Since the gas absorption and emission spectra are caused by scattering, transmission and absorption of electromagnetic energy due to it's molecular structure, the gaseous spectral finger-print is influenced by the following:

Molecular vibration energy—caused by stretching, bending and rotating of chemical molecular bands. This energy is responsible for the IR spectral finger-print of the molecules.

Molecular transfer of electrons energy—caused by breaking/forming chemical bonds, radicals and charged species changing electrons. This energy emitted or absorbed by a molecule is responsible for its UV spectral finger-print.

Gas detection in production area is aimed at explosion threats. Not all gas clouds are hazardous, only if a flammable cloud plume is wide enough to allow flame acceleration to speeds greater than 100 m/see does it become a significant threat. A flame front needs distance to reach the velocities which cause the damaging effects of over-pressure. This distance is mainly controlled by the confinement and congestion of the area.

In typical off-shore industries a gas cloud of 5 meters diameter can be considered a major threat since it can develop an explosion at a low concentration of 2 LEL (stoichiometric cone.). Traditionally, gas cloud monitoring was achieved by installing a grid of many "point" type detectors, in three dimensional grid formation and correlating their signals. One detector seeing gas should cause a warning while a second one would cause automatic actions. However plumes of significant leaks have passed undetected between monitoring positions, and some sensors saturate to become nonresponsive when really needed.

The requirements of point detectors are stringent: a gas has to reach the detector area (surface) at a concentration high enough to cause an alarm. This is quite difficult to accomplish since the gas dilutes in air because of ventilation which is specifically designed in such high risk areas. Also the number of point detectors that can be installed in an area is limited by the machinery space configuration and maintenance. There is also the inherent restriction of the cost benefit of gas detection due mainly to lack of an so effective action of controlling an explosion with an inadequate number of sensors. Add to these restrictions the operational limitations of present catalytic point detectors, the availability of the new emerging optical beam-(remote) detectors was welcomed.

The beam detectors removed the major problem of the point detectors. No more need exists to install a detector close to the leaking source where the plume of the gas is concentrated enough to detect readily.

With the open-path (remote) beam optical detectors, whether the beam ends are close to the source of leak or far away, provided the whole width of the plume is within the beam, the system's response will be similar.

The present status of off-shore high risk area gas and fire protection includes both types of detection approaches. Point IR detection in congested parts where gas may be trapped for some time and the explosion hazard is significant. Beam (open-path) gas detectors in the major air currents (open spacefence line protection).

The advantages and disadvantages of these technologies are summarized in the following.

Point source detectors are advantageous because they are ideal for use in small confined locations such as air intake to control rooms, generator rooms, pump rooms or other isolated pieces of equipment. They quantify the gas concentration at a given location. They are relatively low cost, commonly used and are well recognized by engineers and maintenance stuff. They are characterized by a simple sensor replacement.

Point source detectors are disadvantageous because they do not reflect the actual gas concentration in the entire area. Some types are subject to poisoning by certain materials, such as silicon compounds, mettalo-organies and halogenated compounds. They are characterized by a slow response. They may not reflect actual hazardous conditions in case of high air flowing conditions, it the flow is not directed toward the detector. The gas must reach the specific detector (accuracy will be comprised if the detector is placed incorrectly, or too few are used). Frequent maintenance is required to check calibration. Operating life may be shortened by the presence of persistent background gases. And, in large open space areas, in order to provide adequate coverage a substantial number of detectors is required.

The introduction of spectral signature analysis in point-source detectors (for example IR point detectors) has reduced some of the disadvantages of point source detectors, however the major drawback of local and limited gas measurement still exists with this type of sensor.

Beam (open-path) gas detectors are advantageous because they provide a direct and fast response to changes in gas concentrations. They provide gas surveillance over a large space. They are characterised by fast responses. The speed of response typically ranges between 0.5 and 10 seconds, which is 5–30 times faster than for point detectors. They are more cost-effective than point-type detectors, if the potential release locations are over a large area such as a row of pumps along a pipe rack. They require low maintenance, since equipment is not subject to poisoning. They provide gas release surveillance over a large area. They are unaffected by high background gas levels. They are substantially unaffected by environmental conditions, such as heat, humidity, snow, rain, etc.

Beam (open-path) gas detectors are disadvantageous because they provide average concentration over a short distance (do not give precise concentration at a given location). The beam emitter must be in line of sight with the receiver or reflector (activity in an area may interfere with the beam, leaving an area without detection until the activity stops). Service of some systems can be costly and time consuming, since replacement of failed sensors requires skilled technicians. External radiation sources may hamper their detection capabilities. And, operation may be impaired due to physical obscuration and other conditions that result in more than 90% reduction in beam signal in cases such as very high fog, however, such failures may be automatically revealed.

Today with the emerging novel techniques of electro-optical monitoring that include smart sensors with specific optical filters and microprocessors algorithms that analyze the absorption signal of a gas component within the cluttered signal of changing environment absorption, the open-path remote sensing (beam-sensors) technology has acquired recognition.

Various petrochemical industries, offshore platforms and oil rigs, storage at chemical facilities, fence-line monitoring of chemical, petrochemical and pharmaceutical plant, paint-booths and paint production and storage areas, compressors and pumping stations, liquefied petroleum gas (LPG) and gasoline filing stations, etc., are better protected by the remote sensing optical gas detectors.

EP 0 584389 A1 (and U.S. Pat. No. 5,281,816) teaches a method and system having advantages in some or all of the above respects and particularly useful for detecting the presence of a predetermined hydrocarbon vapour in a monitored area. According to this method gas in or from the monitored area is exposed to radiation emitted from a flashlamp which emits both ultraviolet radiation and infrared radiation; the ultraviolet radiation is detected within a predetermined ultraviolet spectral range, and the infrared radiation is detected within a predetermined infrared spectral range after the radiation emitted from the flashlamp has passed through the gas; and the detected ultraviolet radiation and infrared radiation are compared with a reference of predetermined attenuation characteristics of the hydrocarbon vapour and concentration in the ultraviolet and infrared spectral ranges.

The system according to EP 0 584389 A1 includes a light source, a beamsplitter and two sensors the signal and reference sensors, each includes a light sensitive element and an optical filter. The optical filter of the reference sensor is selected outside, yet close to, the absorption range of the monitored gas, whereas the optical filter of the reference sensor is selected within the absorption range of the monitored gas. The ratio between the signals obtained from both sensors is used to determine the presence or absence of the monitored gas. The beamsplitter ensures that both sensors sense the same field of view and thereby the noise, or in other words, false positive or false negative indications are reduces.

A product in accordance with the teachings of EP 0 584389 A1 is distributed by Spectronix Inc. under the name SAFEYE. The SAFEYE technology analyzes at least two wavelengths within each spectral band, one in a region where the hazardous gas absorbs and one where it does not absorb. The ratio between theses absorption lines when compared to background spectral absorption lines can provide accurate information with regards to gas concentration (absolute or relative) and the location or migration of a cloud (through various lines of sight).

The absorption intensity is related to the concentration (C) of the gas by the Beer-Lambert law:

$$I(\lambda)=I_o(\lambda)e^{-a(\lambda).c.l}$$

where $a(\lambda)$ is the molecular absorption coefficient at $\lambda$ and $l$ is the path length. $I_o(\lambda)$ is the intensity that would be measured in the absence of molecular absorption at $\lambda$.

The optical path is defined by the location of the transmitter (radiation source) and the receiver (sensor) and possible reflectors therebetween. The spectrally selective analyzer can be at either end. If both the transmitter and receiver are collocated, then either a retroreflector or a topographic target is used to reflect the transmitted radiation back to the receiver.

The SAFEYE gas detector includes two parts: a light source and a receiver at a predetermined distance. The system can detect different gases, with respect to different bandpass filters at the absorbing channel signal and the non-absorbing (reference) channel. The signals are analyzed by the microprocessor included in the receiver.

The radiation source is an unique UV-IR pulsating source that can be activated at various frequencies. The very short pulse of light, nsec, enables the recognition of it's unique pattern by the receiver and distinguishes it from background radiation sources such as sunlight, filament lamps, projectors, heat generators, etc. The receiver contains several sensors according to the specific gases (or chemical families) to be detected.

The signal and reference bandpass filters are centered at $\lambda_1$ and $\lambda_2$ in the 3–5 $\mu$m IR band or in the 0.2–0.3 $\mu$m UV band.

The detector is calibrated via a gas cell that is constructed to contain the gas of interest in between the transmitter and receiver. The system analyzes the spectral-finger-print of a chemical (flammable, explosive or toxic gas) in two spectral bands UV and IR where the monitored gases have defined and unique spectral absorption lines. Specific filters are designed for each spectral channel to identify the gases.

The SAFEYE system can provide fast reliable detection of flammable gases (aromatics or paraffins) at lower explosive limit (LEL) levels as well as identification of low concentrations of toxicants at ppm (parts per million) level. The most advanced version incorporates a fire detection option triple IR, which is highly sensitive to small fires at very long distances (4 times the distance of regular optical fire detectors, i.e., 60 m versus existing 15 m ranges).

This open-path, line-of-sight gas detection system can monitor and transmit an alarm signal prior to occurrence of fire or an explosion, identify the chemical family concerned, and activate the required prevention systems.

Reliability and safety being the most important issues when measuring and monitoring combustible or toxic gases, the following performance criteria's must be addressed by the system. Real time measurement (an active system) over a predetermined transmitter receiver path length. Automatic self-calibration to minimize false alarms. Continuous working through significant interference's such as humidity, rain, fog, snow and background radiation (sun, lamps, heaters etc.). Capability to monitor various gas concentrations from traces to potentially explosive levels (PPM to LEL). Immunity to any chemical reaction with hazardous gas environment. Simultaneous detection of homologue hydrocarbons series (C1–C8) with one instrument. Completely immune to industrial and environmental radiation sources. Easily adapted for field usage, simple installation.

The system of the present invention offers improvements to the system and method described in EP 0 584389 A1 in three directions. According to the first, a unique reference optical filter is employed, which improves the performances of the system and method. According to the second, a unique signal optical filter is employed, which renders the system and method particularly sensitive to a specific gas. Whereas according to the third, three (instead of two) sensors are employed, which obviates the need for a beamsplitter. As a result, as detailed hereinbelow, the system according to the present invention is less affected by water and humidity, dust and debris, and other gases which may mask the detection of a preferred gas.

SUMMARY OF THE INVENTION

According to the present invention there are provided method and system for vapour detection.

According to further features in preferred embodiments of the invention described below, provided is a method of detecting the presence of a predetermined vapour of a predetermined concentration in a monitored area, the method comprising the steps of (a) exposing gas in or from the monitored area to radiation at wavelengths at least covering and surrounding from both sides a main absorption peak of the vapour; (b) simultaneously sensing the radiation after passing through the gas by a signal sensor and a reference sensor, each of the sensors including a radiation sensing element, wherein the signal sensor further includes a first optical filter passing wavelengths covering the main absorption peak, yet substantially blocking wavelengths from both sides the main absorption peak of the vapour, whereas the reference sensor further includes a second optical filter passing wavelengths surrounding from both sides the main absorption peak, yet substantially blocking wavelengths covering the main absorption peak of the vapour; and (c) comparing signals obtained from the signal and reference sensors for determining a presence or absence of the vapour of the predetermined concentration in the gas.

According to further features in preferred embodiments of the invention described below, provided is a system for detecting the presence of a predetermined vapour of a predetermined concentration in a monitored area, the system comprising (a) a radiation source for providing radiation at wavelengths at least covering and surrounding from both sides a main absorption peak of the vapour; (b) a signal sensor including a first radiation sensing element and a first optical filter passing wavelengths covering the main absorption peak, yet substantially blocking wavelengths from both sides of the main absorption peak of the vapour; and (c) a reference sensor including a second radiation sensing element and a second optical filter passing wavelengths surrounding from both sides the main absorption peak, yet substantially blocking wavelengths covering the main absorption peak of the vapour; such that simultaneously sensing the radiation after passing through the gas by the signal sensor and the reference sensor and comparing signals obtained from the signal and reference sensors enables determining a presence or absence of the vapour of the predetermined concentration in the gas.

According to further features in preferred embodiments of the invention described below, provided is a method of increasing the sensitivity of detecting the presence of a predetermined first vapour of a predetermined concentration having a first main absorption peak in a monitored area in optional presence of a second vapour having a second, yet close, main absorption peak, the method comprising the steps of (a) exposing gas in or from the monitored area to radiation at wavelengths at least covering and surrounding from both sides the main absorption peaks of the vapours; (b) simultaneously sensing the radiation after passing through the gas by a signal sensor and a reference sensor, each of the sensors including a radiation sensing element, wherein the signal sensor further includes a first optical filter passing wavelengths covering the first main absorption peak, yet substantially blocking wavelengths surrounding from both sides the first main absorption peak and wavelengths covering the second main absorption peak, whereas the reference sensor further includes a second optical filter passing wavelengths surrounding from both sides the first main absorption peak, yet substantially blocking wavelengths covering the first and second main absorption peaks; and (c) comparing signals obtained from the signal and reference sensors for determining a presence or absence of the first vapour of the predetermined concentration in the gas.

According to further features in preferred embodiments of the invention described below, provided is a system for increasing the sensitivity of detecting the presence of a predetermined first vapour of a predetermined concentration having a first main absorption peak in a monitored area in optional presence of a second vapour having a second, yet close, main absorption peak, the system comprising (a) a radiation source for providing radiation at wavelengths at least covering and surrounding from both sides the main absorption peaks of the vapours; (b) a signal sensor including a first radiation sensing element and a first optical filter passing wavelengths covering the first main absorption peak, yet substantially blocking wavelengths surrounding from both sides the first main absorption peak and wavelengths covering the second main absorption peak; and (c) a reference sensor including a second radiation sensing element and a second optical filter passing wavelengths surrounding from both sides the first main absorption peak, yet substantially blocking wavelengths covering the first and second main absorption peaks; such that simultaneously sensing the radiation after passing through the gas by the signal sensor and the reference sensor and comparing signals obtained from the signal and reference sensors enables determining a presence or absence of the first vapour of the predetermined concentration in the gas.

According to still further features in the described preferred embodiments a beamsplitter is employed for splitting the radiation after passing through the gas into the signal and reference sensors, such that both the signal and reference sensors sense a single field of view.

According to still further features in the described preferred embodiments the first filter includes a first substance passing radiation at wavelengths covering the first main absorption peak and a second substance substantially blocking radiation at wavelengths covering the second main absorption peak.

According to further features in preferred embodiments of the invention described below, provided is a method of detecting the presence of a predetermined vapour of a predetermined concentration in a monitored area, the method comprising the steps of (a) exposing gas in or from the monitored area to radiation at wavelengths at least covering and surrounding from both sides a main absorption peak of the vapour; (b) simultaneously sensing the radiation after passing through the gas by three independent sensors including at least one signal sensor and at least one reference sensor, each of the three sensors including a radiation sensing element, wherein at least one of the at least one signal sensors further includes a first optical filter passing wavelengths covering the main absorption peak, yet substantially blocking wavelengths from both sides of the main absorption peak of the vapour, whereas each of the at least one reference sensor further includes a second optical filter passing wavelengths being close from at least one side to the main absorption peak, yet substantially blocking wavelengths covering the main absorption peak of the vapour; and (c) comparing signals obtained from the sensors for determining a presence or absence of the vapour of the predetermined concentration in the gas, thereby obviating the need for a beamsplitter. Signals comparison and analysis is effected by a dedicated algorithm which is further described hereinbelow.

According to further features in preferred embodiments of the invention described below, provided is a system for detecting the presence of a predetermined vapour of a predetermined concentration in a monitored area, the system comprising (a) a radiation source for providing radiation at wavelengths at least covering and surrounding from both sides a main absorption peak of the vapour; (b) three independent sensors including (i) at least one signal sensor, each of the at least one signal sensors including a first radiation sensing element and a first optical filter passing wavelengths covering the main absorption peak, yet substantially blocking wavelengths from both sides of the main absorption peak of the vapour; and (ii) at least one reference sensor, each of the at least one reference sensors including a second radiation sensing element and a second optical filter passing wavelengths being close from at least one side to the main absorption peak, yet substantially blocking wavelengths covering the main absorption peak of the vapour; such that simultaneously sensing the radiation after passing through the gas by the three independent sensors and comparing signals obtained from the sensors enables determining a presence or absence of the vapour of the predetermined concentration in the gas, and obviates the need for a beamsplitter.

According to still further features in the described preferred embodiments the radiation is effected via a radiation source selected from the group consisting of a flashlamp and a modulated filament lamp.

According to still further features in the described preferred embodiments the flashlamp is a quartz Xenon flashlamp.

According to still further features in the described preferred embodiments the second filter passes wavelengths surrounding from both sides the main absorption peak, yet substantially blocking wavelengths covering the main absorption peak of the vapour.

According to still further features in the described preferred embodiments the second filter is a notch filter.

According to still further features in the described preferred embodiments the notch filter includes a first substance passing radiation at wavelengths covering and surrounding from both sides the main absorption peak and a second substance substantially blocking radiation at wavelengths covering the main absorption peak.

According to still further features in the described preferred embodiments the three sensors include two units of the reference sensor and a single unit of the signal sensor.

According to still further features in the described preferred embodiments the three sensors include two units of the signal sensor and a single unit of the reference sensor.

According to still further features in the described preferred embodiments the three sensors include two signal sensors, one of the signal sensors further includes a third optical filter passing wavelengths covering a second main absorption peak of the vapour, yet substantially blocking wavelengths from both sides of the second main absorption peak of the vapour.

According to still further features in the described preferred embodiments the comparison is accompanied by a re-zeroing procedure in which zero ratios of signals obtained from the signal and reference sensors are redefined in accordance with non-vapour spectral disturbances.

According to still further features in the described preferred embodiments the three sensors include two signal sensors, one of the signal sensors further includes a third optical filter passing wavelengths covering a second main absorption peak of the vapour, yet substantially blocking wavelengths surrounding from both sides the second main absorption peak of the vapour.

According to still further features in the described preferred embodiments a window being substantially transparent to the radiation and positioned in front of each of the at least one reference sensors is provided.

According to still further features in the described preferred embodiments a housing is provided formed with windows being substantially transparent to the radiation and positioned in front of each of the three sensors, the widows being covered with a water repellent material.

According to still further features in the described preferred embodiments of the invention provided is a reference sensor for vapour detection comprising a radiation sensing element and an optical filter passing wavelengths surrounding from both sides a main absorption peak of the vapour, yet substantially blocking wavelengths covering the main absorption peak of the vapour.

According to still further features in the described preferred embodiments of the invention provided is a signal sensor for detection of a first vapour in presence of a second vapour comprising a radiation sensing element and an optical filter passing wavelengths covering a first main absorption peak of the first vapour, yet substantially blocking wavelengths surrounding from both sides the first main absorption peak and wavelengths covering a second main absorption peak of the second vapour.

The present invention successfully addresses the shortcomings of the presently known configurations by providing improvements to the prior art in the filters employed both in the reference and signal sensors and by increasing the number of sensors employed, which obviates the use of a beamsplitter. The present invention improves detection performances under extreme and harsh weather conditions such as, but not limited to, heavy rain, mist (water spare), fog, partial obscuration by accumulated dirt and dust, etc.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
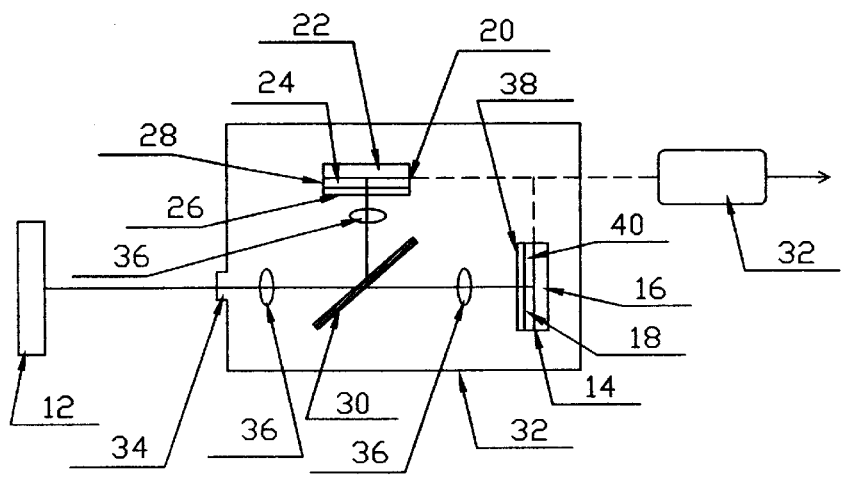
FIG. 1 is a schematic depiction of one embodiment of the system according to the present invention.

The present invention is of a method and system which can be used for detecting the presence of predetermined gases or vapours in a monitored area. Specifically, the present invention can be used for detecting flammable hydrocarbon vapours when they are present at a concentration which might indicate a possible flammable or explosive atmosphere, and the invention is therefore described primarily with respect to this application.

The method and system according to the present invention are particularly useful for detecting flammable hydrocarbon vapours in a hazardous area, e.g., petrochemical industry facilities, offshore platforms and oil rigs, storage areas at chemical facilities, fence-line monitoring of chemical, petrochemical and pharmaceutical plants, paint-booths and paint production and storage areas, compressors and pumping stations, liquefied petroleum gas (LPG) and gasoline filing stations, etc. Such a detection is very important to provide a signal or alarm of a hazardous condition, or to automatically actuate a fire extinguishing system or other control in order to remove the hazardous condition.

The principles and operation of a method and system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The method and system according to the present invention serve for detecting the presence of a predetermined vapour of a predetermined concentration in a monitored area.

The term "vapour" is used herein in the specification and in the claims section below to indicate a gas state. The gas state may either be native, i.e., of a material which is gaseous at ambient temperature, or due to evaporation of certain liquids. The vapour may be of any type.

In particular the vapour and its concentration are those that may cause an atmosphere to become flammable, explosive or toxic as has been determined, for example, by the U.S. "Clean Air Act", which is incorporated by reference as if fully set forth herein. The "Clean Air Act" lists toxic and hazardous gases, some of which are also flammable.

Examples of vapours which may be detected according to the present invention include paraffin and aromatic hydrocarbons, such as, but not limited to, methane, ethane, propane, pentane, hexane, benzene, toluene, tetralin and xylene, halogenated acids, such as HCl, HBr, HI, halocarbons and chloro-fluoro-carbons (CFC's) and other evaporative or gaseous substances, such as, but not limited to, hydrogen sulfide ($H_2S$), sulfur oxide ($SO_2$), ammonia ($NH_3$), amines ($NH_2$-R, where R stands for a hydrocarbon backbone), nitrous compounds ($NO_x$), carbon mono-oxide (CO), carbon di-oxide ($CO_2$), etc.

Referring now to the drawings, FIG. 1 illustrates one embodiment of a system according to the present invention, which is referred to hereinbelow a system 10.

Thus, system 10 includes a radiation source 12. Radiation source 12 provides radiation at wavelengths at least covering and surrounding from both sides a main absorption peak of the vapour to be detected.

Figure 2:
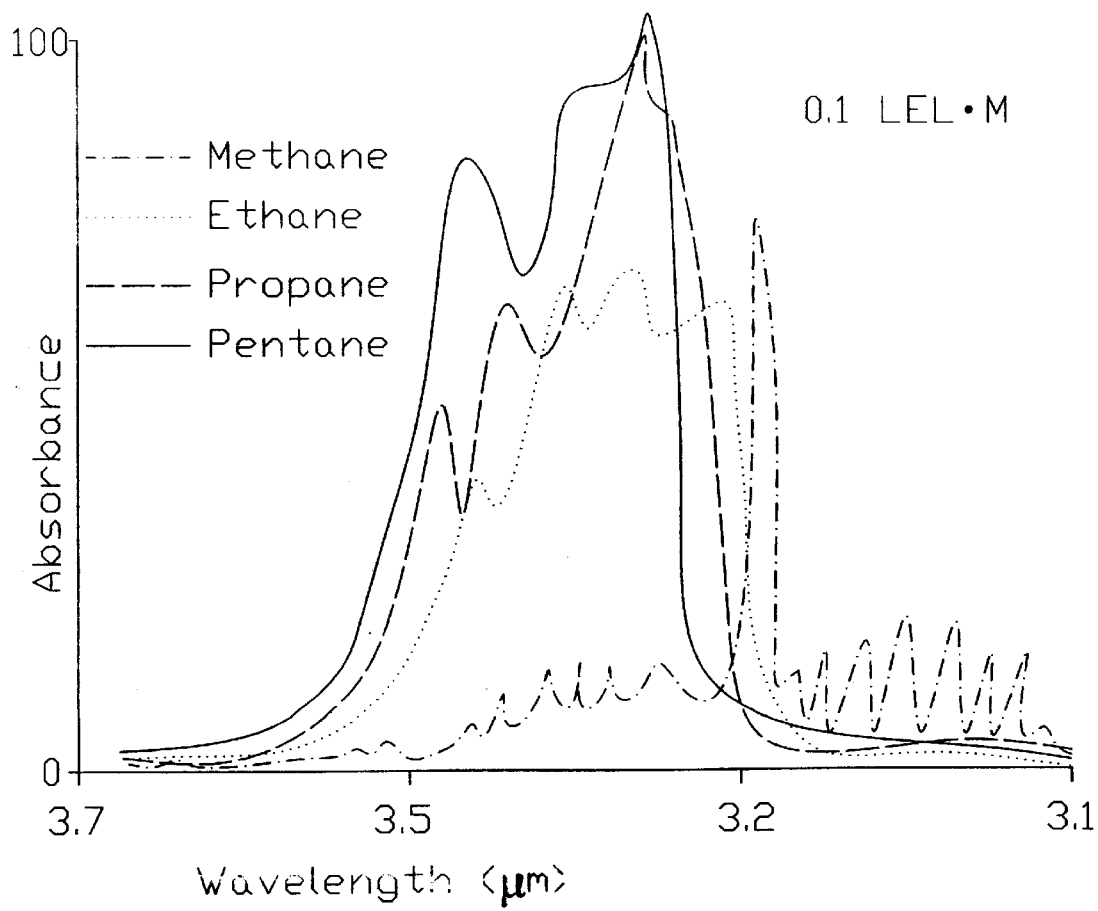
FIG. 2 presents absorbance plots of few hydrocarbon vapours.

It is well known in the art that different gases have spectral signatures (finger-print) at different spectral ranges. Hydrocarbons, for example, have main absorption peaks both in the UV and in the IR spectral ranges. According to the present invention any of the main absorption peaks of any vapour may be analyzed. For example, FIG. 2 shows the absorption spectra of methane, ethane, propane and pentane in the IR range. The main peak of absorption of methane, for example, is at about 3.32 $\mu$m and is relatively narrow. The main peaks of the other vapours are substantially wider and include some minor peaks.

Typically the radiation source would have a much broader spectral range, for example, from short UV radiation through the visible and IR ranges and up to the microwave range. A suitable radiation source according to the present invention is, for example, a flashlamp, such as a quarts Xenon flashlamp, or a modulated filament lamp. The advantages of these radiation sources, which provide pulsative radiation patterns, are listed in EP 0 584389 A1, which is incorporated by reference as if fully set forth herein.

System 10 further includes a signal sensor 14. Sensor 14 includes a first radiation sensing element 16.

The term "radiation sensing element" is used herein to indicate an element which is capable of transforming a radiation intensity into an analog or digital signal, itself proportionate to the radiation intensity. The proportion may be different for different wavelengths. The spectral range of the element is selected according to the spectral range employed for gas detection. A suitable element for the visible through the IR spectral ranges includes, for example, a led-selenide (PbSe), led-sulfate (PbS) or pyroelectric crystals, which changes their conductivity in response to radiation in the appropriate spectral range, according to a well defined spectral response curve.

Sensor 14 further includes a first optical filter 18. Filter 18 is designed to pass radiation in wavelengths covering the main absorption peak of the vapour to be detected, yet to substantially block wavelengths from both sides of the main absorption peak of the vapour to be detected. Thus, for methane, for example, filter 18 is selected to pass radiation having wavelengths of about 3.30–3.34 $\mu$m and to substantially block any radiation outside this spectral range.

System 10 further includes a reference sensor 20. Like sensor 14, sensor 20 includes a second radiation sensing element 22. Sensor 20 further includes a second optical filter 24. Filter 24 is designed to pass wavelengths surrounding from both sides the main absorption peak, yet to substantially block wavelengths covering the main absorption peak of the vapour to be detected.

The term "surrounding" as used herein refers to or within the close surrounding. The surrounding extremes are preferably within at least ±0.8 μm, more preferably within at least ±0.5 μm, yet more preferably within at least ±0.4 μm, most preferably within at least ±0.3 μm or less from the center of the main peak, depending on the vapour of choice.

Thus, for methane, for example, filter 24 is selected to pass radiation having wavelengths of about 3.28–3.30 μm and about 3.34–3.36 μm (the surrounding range), and to substantially block any radiation in the 3.30–3.34.

According to a preferred embodiment of the invention second filter 24 is a notch filter, having a notch in the range of main absorption of the vapour to be detected. Such a filter may be prepared by layering a first substance 26 designed to pass radiation at wavelengths covering and surrounding from both sides the main absorption peak of the vapour and a second substance 28 designed to substantially block radiation at wavelengths covering the main absorption peak of the vapour to be detected.

Figure 3:
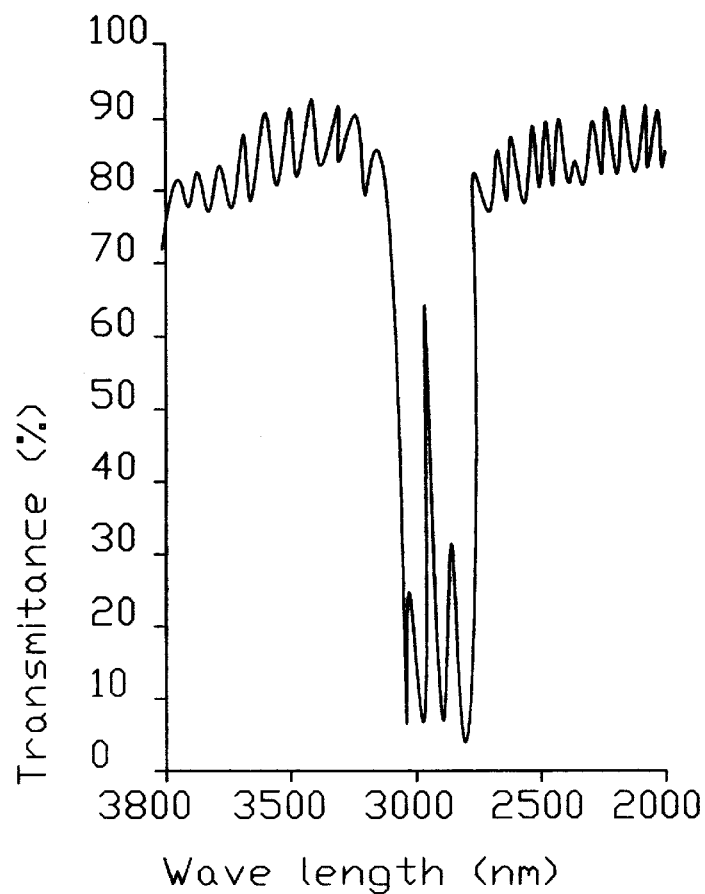
FIG. 3 presents a plot of polystyrene transmitance spectrum in the mid IR range.

Thus, for methane, for example, substance 26 of filter 24 is selected to pass radiation having wavelengths of about 3.28–3.36 μm and to substantially block any radiation outside this range, whereas substance 28 of filter 24 is selected to substantially block radiation in the 3.30–3.34 spectral range. In this case substance 28 may be a layer of polystyrene. FIG. 3 presents the transmitance spectrum of polystyrene at the IR range. Compare to the spectrum of methane shown in FIG. 2.

Simultaneously sensing the radiation after passing through the gas by signal sensor 14 and reference sensor 20, and comparing signals obtained from these sensors enables the system according to the present invention to determine a presence or absence of the vapour of the predetermined concentration is the gas monitored.

Comparison is preferably effected by calculating a ratio of the signals obtained by the sensors. Assume, for example, the ratio S/R, where S is the signal obtained from the signal sensor and R is the signal obtained from the reference sensor. When no vapour is present, the ratio S/R is expected to be 1, whereas if vapour is present the ratio is expected to decrease because S decreases whereas R is remained substantially unchanged.

According to a preferred configuration of the present embodiment of the invention system 10 further includes a beamsplitter 30. Beamsplitter 30 serves for splitting the radiation after passing through the gas including the vapour to be detected into signal 14 and reference 30 sensors, such that both sensors sense a single field of view, which ensures that non-vapour associated attenuations, due to, for example, mist, rain, snow, dust, background radiation, etc., will affect both sensors substantially to the same degree, thereby the chance for a false alarm is reduced.

System 10 preferably further includes a housing 32 equipped with a window 34 facing radiation source 12. Housing 32 serves for protecting sensors 14 and 20. Window 34 may be an opening. However, according to a preferred embodiment of the invention window 34 is made of a material transparent to the radiation employed. For example, for radiation in the IR range a sapphire window is preferably selected, whereas for radiation in the UV range a quartz window is preferably selected.

System 20 may further include lenses 36 which serve for focusing the radiation onto beamsplitter 30 and/or sensors 14 and 20.

In addition, system 20 may include reflectors to direct radiation emitted from source 12 into window 34, so as to create an optical path (e.g., zig-zag) having an effective coverage of the monitored area.

The signals or output of sensors 14 and 20 are directed, as indicated by dotted lines, to a control logic circuitry 37, which outputs control signals to an indicator or alarm unit and/or to a fire extinguisher unit, all as further described in EP 0 584389 A1.

Figure 6:
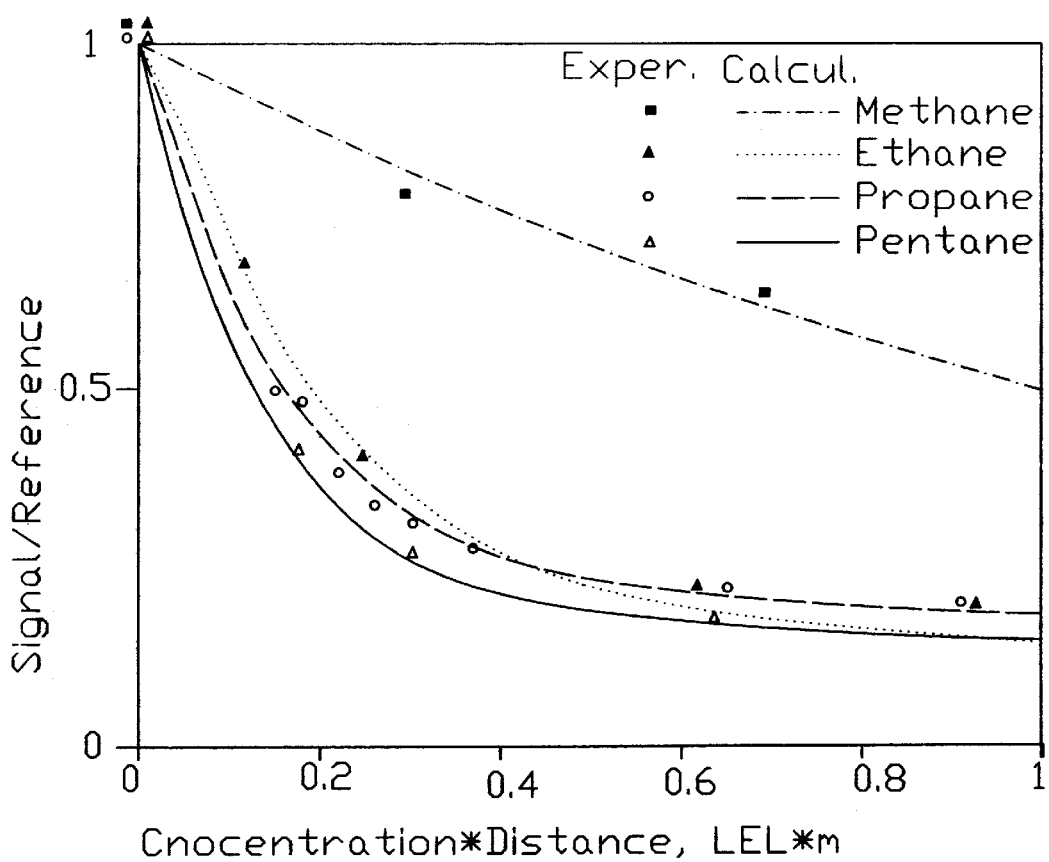
FIG. 6 present vapour concentration determinations of the hydrocarbon vapours of FIG. 2.

Control logic circuitry 37 includes data and follows the Beer-Lambert Law which enables circuitry 37 to determine weather a critical gas concentration (e.g., LEL, TLV) has been senses. Further detail concerning circuitry 37 are provided in EP 0 584389 A1. FIG. 6 presents vapour concentration determination experiments for few hydrocarbon vapours made with the system according to the present invention.

System 10 was so far described as having an open path. However, it is clear that system 10 may include a sample cell, as described, for example, in EP 0 584389 A1, and also serve as a point detector as further described in the Background section above.

System 10 differs from the system disclosed in EP 0 584389 A1 in the filter used within the reference sensor.

EP 0 584389 A1 teaches a reference optical filter designed to pass radiation in wavelengths outside, yet close to, one side (as opposed to both sides) of the main absorption peak of the vapour to be detected.

In sharp distinction, according to this embodiment of the present invention wavelengths on both sides of (i.e., surrounding) the main absorption peak of the vapour to be detected are passed by the filter used for referencing.

As was experimentally determined, this, in turn, is a crucial distinction, which improves the performances of the gas detector according to the present invention as compared with the prior art gas detector, and reduces false alarm incidents to a great degree.

It is believed that the improvement in performances is due to the following. Spectral emission, absorption and response are characterized by peaks of emission, absorption or response, respectively, wherein each peak is accompanied by a descending and an acceding tail or shoulder.

It is very rare, if not theoretical, to have a plateau spectral behavior over extended ranges.

Although the reference and the signal optical filters are selected to be close in spectral ranges of transmitance, they are still different. Therefore, any spectral phenomenon, especially a changing or transient spectral phenomena (disturbance), having a tail or shoulder in the spectral range covered by both filters would affect their respective radiation sensitive elements in a different fashion, not to mention that the spectral response curves of the elements themselves is typically characterized by being descending or ascending in the spectral range employed.

Therefore, by referencing on both sides of the main peak of the vapour to be detected one averages the effects of these spectral phenomena or disturbances.

Spectral phenomena or disturbances of such behavior include, but are not limited to, the spectral emission of the radiation source which may change with age and temperature; the spectral emission of external sources (e.g., sun light, lighting bodies, etc.); the spectral absorption of and/or scattering caused by mist, rain, snow and dust; and, as already mentioned, the spectral response of the radiation sensitive elements.

Thus, further according to the present invention provided is a method of detecting the presence of a predetermined vapour of a predetermined concentration in a monitored area. The method includes the following steps.

First, gas in or from the monitored area is exposed to radiation at wavelengths at least covering and surrounding from both sides a main absorption peak of the vapour.

Second, after passing through the gas the radiation is simultaneously sensed by a signal sensor and a reference sensor. Each of the sensors includes a radiation sensing element, wherein the signal sensor further includes a first optical filter passing wavelengths covering the main absorption peak, yet substantially blocking wavelengths from both sides of the main absorption peak of the vapour, and the reference sensor further includes a second optical filter passing wavelengths surrounding from both sides the main absorption peak, yet substantially blocking wavelengths covering the main absorption peak of the vapour.

Finally, signals obtained from the signal and reference sensors are compared and a presence or absence of the vapour of the predetermined concentration in the gas being monitored is determined.

According to another embodiment of the present invention provided are method and system for increasing the sensitivity of detecting the presence of a predetermined first vapour of a predetermined concentration having a first main absorption peak in a monitored area, in optional presence of a second vapour having a second, yet close, partially overlapping, main absorption peak.

This situation is emphasized, for example, in FIG. 2. Note, for example, that the main peak of propane partially overlaps that of methane.

The basic construction of the system according to this embodiment is similar to that shown in FIG. 1 and described hereinabove. The differences, which are described hereinbelow, reside in the construction of the optical filter deployed in the signal filter.

Thus, the system according to this embodiment of the invention includes a radiation source for providing radiation at wavelengths at least covering and surrounding from both sides the main absorption peaks of both vapours.

The system further includes a signal sensor which includes a first radiation sensing element and a first optical filter passing wavelengths covering the main absorption peak, yet substantially blocking wavelengths from both sides of the first main absorption peak and further blocking wavelengths covering the second main absorption peak.

The system further includes a reference sensor which includes a second radiation sensing element and a second optical filter passing wavelengths surrounding from both sides the main absorption peak, yet substantially blocking wavelengths covering the first and second main absorption peaks.

Simultaneously sensing the radiation after passing through the gas by the signal sensor and the reference sensor and comparing signals obtained from the signal and reference sensors enables determining a presence or absence of the first vapour of the predetermined concentration is the gas.

As mentioned above, according to this embodiment of the invention, the first filter (i.e., that of the signal sensor),
which is indicated by numerical reference 18 in FIG. 1, passes wavelengths covering the first main absorption peak of the first vapour, say methane, yet substantially blocking wavelengths surrounding from both sides the first main absorption peak and further blocking wavelengths covering the second main absorption peak of the second vapour, say propane.

According to a preferred configuration of this embodiment of the present invention filter 18 includes a first substance 38 passing radiation at wavelengths covering the first main absorption peak and a second substance 40 substantially blocking radiation at wavelengths covering the second main absorption peak.

In the case where the second main absorption peak is of propane, and the spectral range is IR, polypropylene may be a second substance of choice.

Figure 4:
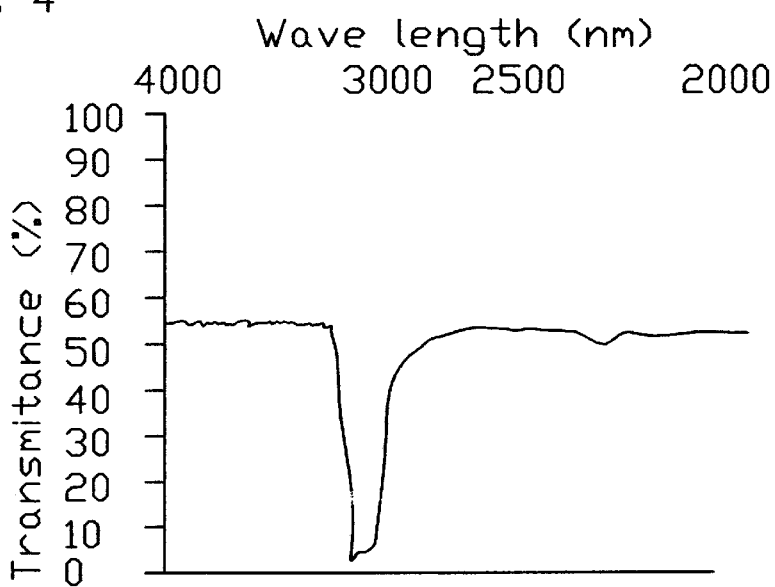
FIG. 4 presents a plot of polyethylene transmitance spectrum in the mid IR range.

FIG. 4 presents the transmitance spectrum of polypropylene at the IR range. Compare to the spectrum of propane shown in FIG. 2.

The method according to this embodiment of the invention includes to the following steps.

First, gas in or from the monitored area is exposed to radiation at wavelengths at least covering and surrounding from both sides the main absorption peaks of the vapours.

Second, after passing through the gas the radiation is simultaneously sensed by a signal sensor and a reference sensor. Each of the sensors includes a radiation sensing element, wherein the signal sensor further includes a first optical filter passing wavelengths covering the first main absorption peak, yet substantially blocking wavelengths surrounding from both sides the first main absorption peak and wavelengths covering the second main absorption peak, whereas the reference sensor further includes a second optical filter passing wavelengths surrounding from both sides the first main absorption peak, yet substantially blocking wavelengths covering the first and second main absorption peaks.

Finally, signals obtained from the signal and reference sensors are compared for determining a presence or absence of the first vapour of the predetermined concentration is the gas.

Figure 5:
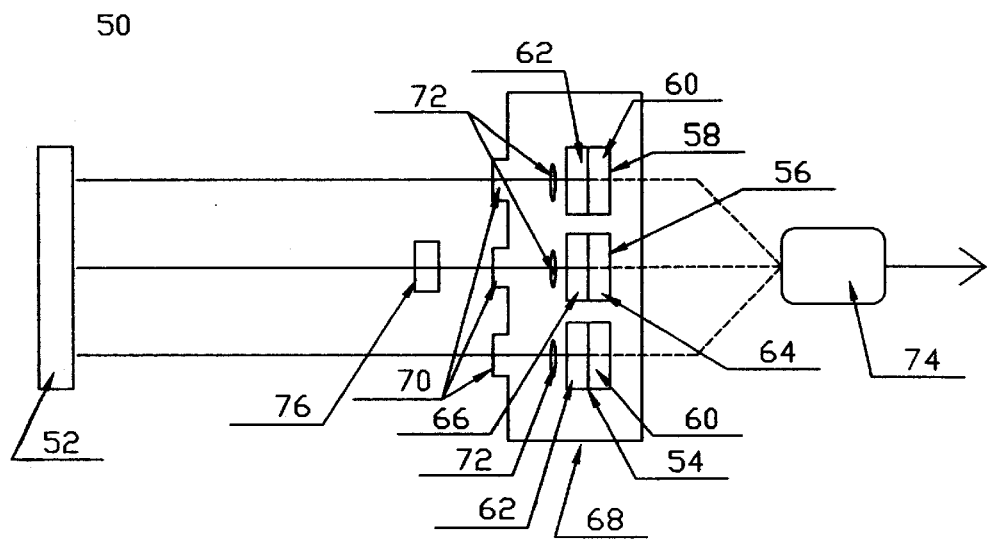
FIG. 5 is a schematic depiction of another embodiment of the system according to the present invention.

As shown in FIG. 5, according to another embodiment of the present invention provided is another system for detecting the presence of a predetermined vapour of a predetermined concentration in a monitored area, which is referred to hereinbelow as system 50.

Like system 10, system 50 includes a radiation source 52 for providing radiation at wavelengths at least covering and surrounding from o both sides a main absorption peak of the vapour to be detected. However, in contrast with system 10 and with the system described in EP 0 584389 A1, system 50 includes three (as opposed to two) independent sensors 54, 56 and 58.

Of the three sensors, according to one embodiment two, say 54 and 58, are reference sensors, whereas the third, say 56, is a signal sensor, whereas according to another embodiment, one sensor, say 56, is a reference sensor, whereas the other two sensors, say 54 and 58, are signal sensors.

The reference sensor(s) according to this embodiment of the invention are either of a prior art type, as described in EP 0 584389 A1, or preferably include a notch filter as described hereinabove with respect to system 10.

Thus, according to this embodiment of the invention system 50 includes at least one signal sensor, say two, 54 and 58. Each of signal sensors 54 and 58 includes a first radiation sensing element 60 and a first optical filter 62. Filters 62 pass wavelengths covering the main absorption peak, yet substantially block wavelengths from both sides of the main absorption peak of the vapour to be detected.

System 50 further includes at least one reference sensor, say one, 56, which includes a second radiation sensing element 64, and a second optical filter 66. Filter 66 passes wavelengths close from at least one side to the main absorption peak, yet substantially blocks wavelengths covering the main absorption peak of the vapour to be detected.

Like system 10, system 50 preferably includes a housing 68 formed with windows 70. As before lenses 72 may be employed to focus the radiation into housing 68.

Simultaneously sensing the radiation after passing through the monitored gas by the three independent sensors and comparing signals obtained from the sensors enables to determine a presence or absence of the vapour of the predetermined concentration is the gas.

It is important to note that the use of three sensors obviates the need for a beamsplitter. This is the case since the results are double checked and only if consistency in the results is obtained the vapour is declared as present or absent.

This is of great importance since avoiding a beamsplitter broadens the field of view and, as a direct result, the system is less subjected to misalignments.

The signals or output of the sensors are directed, as indicated by dotted lines, to a control logic circuitry 74, which outputs control signals to an indicator or alarm unit and/or to a fire extinguisher unit, all as further described in EP 0 584389 A1 and hereinabove.

Control logic circuitry 74 includes data and follows the Beer-Lambert Law which enables circuitry 74 to determine weather a critical gas concentration has been senses. Further detail concerning circuitry 74 are provided in EP 0 584389 A1 and hereinbelow.

Comparison is preferably effected via circuitry 74 by calculating a ratio of the signals obtained by the sensors. Assume, for example, the ratios Q01 and Q02 which reflect the ratios between the signal obtained from the first signal sensor and the reference sensor and the signal obtained from the second signal sensor and the reference sensor, respectively.

When no vapour is present the ratios Q01 and Q02 are expected both to be equal, whereas if vapour is present the ratios are expected to decrease because the signal readings decrease whereas the reference reading is remained substantially unchanged.

However, in any case, the change in the ratios S1/R and S2/R is expected to be similar. If the change is not similar, it is a strong indication that the change is due to a spectral disturbance and not due to detection of the vapour.

In field experemintations it was found that under wet conditions (e.g., rain) which forms drops on the surface of windows 70 which scatter IR radiation, since each of the sensors employed senses a different field of view the number of false alarms was increased. Two solutions were therefore devised to overcome the problem.

According to the first, the windows are covered with a water repellent substance which is transparent to the spectral range employed. A suitable substance in the IR range is a fluorocarbon polymer (e.g., TEFLON by DuPont).

According to the second, a second window(s) 76 was added in front of the reference sensor(s) 56. The addition of a second window doubles the statistical amount of water present in the optical path leading to the reference sensor(s), such that under wet conditions the signal(s) generated by the reference sensor(s) is statistically decreased to a greater degree as compared with the signal sensors. As a result the number of false alarms was tremendously reduced.

When two signal sensors are employed, it is, in some cases, preferred to have one of the signal sensors include an optical filter passing wavelengths covering a second main absorption peak of the vapour (e.g., in the UV spectral range or one IR range as opposed to another IR range), yet substantially blocking wavelengths from both sides of the second main absorption peak of the vapour. In this case the single reference sensor serves both signal sensors and the radiation source is selected to provide radiation in all required spectral ranges. A quartz Xenon flashlamp is a suitable radiation source.

It will be appreciated that water has a main absorption peak in the 2–3 micrometers spectral range, hydrocarbons have main absorption peaks in the 3–4 micrometer spectral range, whereas gases such as CO has a main absorption peak in the 4–5 micrometer spectral range. Thus, selecting different signal sensors which are sensitive in these different spectral ranges may assist in differentiating among spectral events.

The method according to this embodiment of the invention includes the following steps.

First, gas in or from the monitored area is exposed to radiation at wavelengths at least covering and surrounding from both sides a main absorption peak of the vapour.

Second, after passing through the gas the radiation is simultaneously sensed by three independent sensors including at least one signal sensor and at least one reference sensor. Each of the three sensors includes a radiation sensing element. At least one of the signal sensors further includes a first optical filter passing wavelengths covering the main absorption peak, yet substantially blocking wavelengths from both sides of the main absorption peak of the vapour to be detected. Each of the reference sensors further includes a second optical filter passing wavelengths being close from at least one side to the main absorption peak, yet substantially blocking wavelengths covering the main absorption peak of the vapour.

Finally, signals obtained from the sensors are compared for determining a presence or absence of the vapour of the predetermined concentration is the gas, thereby obviating the need for a beamsplitter.

When system 50 is constructed having an open path, control logic circuitry 74 preferably includes an automatic gain control (AGC) unit which compensates for environmental spectral disturbances. The automatic gain control executes an algorithm that identifies ratio changes associated with non-vapour effects or spectral disturbances such as rain.

Thus, system 50 includes three operation states which are automatically dictated by circuitry 74 according to the following rules.

Basically, re-zeroing procedures are employed to ensure that spectral disturbances would not be interpreted as vapour detection.

Define "zero ratios", Q01 and Q02, as the ratios between the signals obtained from the two signal sensors 1 and 2, respectively, and the reference sensor at calibration under ideal conditions.

Define "normalized ratios" N1 and N2 as the ratios between presently measured ratios, M1 and M2 and Q01 and Q02, respectively. When vapour is below its predetermined concentration and no spectral disturbances are experienced both N1 and N2 are expected to equal 1.

In a normal operation state the zero ratios, Q01 and Q02, serve as such as long as the N1 and N2 ratios remain unchanged within a predetermined range (e.g., ±10%). Vapour detection in the normal state is reported when both N1 and N2 decrease substantially in parallel under a threshold value, say under 80% of their original value.

However, due to spectral disturbance a "non-vapour" effect may take place. A non-vapour effect may be (i) rise in the signal obtained from the reference sensor; (ii) above threshold decrease in N1 (or N2) which is not accompanied by a similar decrease in N2 (or N1); and (iii) increase of N1 and/or N2.

In case a "non-vapour" effect takes place a re-zeroing procedure is initiated under a second state of operation. In the second state new zero ratios are defined, Q01' and Q02', as the ratios between the signals obtained from the two signal sensors 1 and 2 and the reference sensor under the present conditions.

When a predetermined time period, say one hour, elapses while in the second state, and no re-zeroing event had taken place, the normal state is resumed wherein the new zero ratios, Q01' and Q02', permanently replace the old ratios, Q01 and Q02, as long as the resumed normal state is effective. Furthermore, the acting normal state ratios are recorded into a permanent memory (e.g., every hour) and are re-employed each time the detector is turned from off to on state. In addition, the signal received from the reference sensor under normal operation conditions, as these conditions may be redefined periodically as described above, is also recorded in the permanent memory as $R_{ref}$, such that it is available upon turning the detector on.

Thus, the system may alternately operate under the normal or second states of operation according to the spectral disturbances it faces. In both cases, due to the re-zeroing procedure herein described the system can detect vapours if present above the predetermined concentration.

If while in the second state frequent "non-vapour" effects take place (e.g., 10 events per minute), a dangerous situation may arise in which the system zeros in the presence of a detectable amount of vapour. To avoid such a situation a third operation state is effected in which the normalized ratio is calculated over a prolonged period of time (averaged over a plurality of radiation pulses).

Furthermore, in the third operation state a Q01' and Q02' are defined as a function of the last normal zero ratios and the ratio between Rref and is the signal presently received from the reference sensor (R).

For example:

$$Q0(1,2)'' = \frac{Q0(1,2)[X + (1-X)(R/R_{ref})]}{(R/R_{ref})}$$

where X is the predetermined allowable deviation range (e.g., 0.1).

While at the third operation state, the detector continues to calculate the Q01' and Q02' ratios. After a predetermined period of time devoid of frequent "non-vapour" effects, the detector re-resumes the second operation state, wherein the zero ratios employed are Q01' and Q02' which were continuously calculated while in the third state of operation under the rules of the second state of operation described hereinabove.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of increasing the sensitivity of detecting the presence of a predetermined first vapour of a predetermined threshold concentration having a first main absorption peak in a monitored area in optional presence of a second vapour having a second, yet close, main absorption peak, the method comprising the steps of:

(a) exposing gas at the monitored area to radiation at wavelengths at least covering and surrounding from both sides said main absorption peaks of the vapours;

(b) simultaneously sensing said radiation after passing via an open path through said gas by three independent sensors including a signal sensor, a reference sensor and an additional sensor identical to said signal or to said reference sensor, each of said three sensors including a radiation sensing element, wherein said signal sensor further includes a first optical filter passing wavelengths covering said first main absorption peak, yet substantially blocking wavelengths from both sides said first main absorption peak and wavelengths covering said second main absorption peak, whereas said reference sensor further includes a second optical filter passing wavelengths surrounding from both sides said first main absorption peak, yet substantially blocking wavelengths covering said first and second main absorption peaks; and (c) comparing signals obtained from said three sensors for determining a presence or absence of the first vapour of the predetermined concentration in said gas.

2. The method of claim 1, wherein said radiation is effected via a radiation source selected from the group consisting of a flashlamp and a modulated filament lamp.

3. The method of claim 2, wherein said flashlamp is a quarts Xenon flashlamp.

4. The method of claim 1, wherein said second filter is a notch filter.

5. The method of claim 4, wherein said notch filter includes a first substance passing radiation at wavelengths covering and surrounding from both sides said first main absorption peak and a second substance substantially blocking radiation at wavelengths covering said first main absorption peak.

6. The method of claim 1, wherein said first filter includes a first substance passing radiation at wavelengths covering said first main absorption peak and a second substance substantially blocking radiation at wavelengths covering said second main absorption peak.

7. A method of detecting the presence of a predetermined vapour of a predetermined threshold concentration in a monitored area, the method comprising the steps of:

(a) exposing gas at the monitored area to radiation at wavelengths at least covering and surrounding from both sides a main absorption peak of the vapour;

(b) simultaneously sensing said radiation after passing via an open path through said gas by three independent sensors including a signal sensors, a reference sensor and an additional sensor identical to said signal or to said reference sensor, each of said three sensors including a radiation sensing element, wherein said signal sensor further includes a first optical filter passing wavelengths covering said main absorption peak, yet substantially blocking wavelengths from both sides of said main absorption peak of the vapour, whereas said reference sensor further includes a second optical filter passing wavelengths being close from at least one side to said main absorption peak, yet substantially blocking wavelengths covering said main absorption peak of the vapour; and (c) comparing signals obtained from said three sensors for determining a presence or absence of the vapour of the predetermined concentration in said gas, thereby obviating the need for a beamsplitter.

8. The method of claim 7, wherein said radiation is effected via a radiation source selected from the group consisting of a flashlamp and a modulated filament lamp.

9. The method of claim 8, wherein said flashlamp is a quarts Xenon flashlamp.

10. The method of claim 7, wherein said second filter passes wavelengths surrounding from both sides said main absorption peak, yet substantially blocking wavelengths covering said main absorption peak of the vapour.

11. The method of claim 10, wherein said second filter is a notch filter.

12. The method of claim 11, wherein said notch filter includes a first substance passing radiation at wavelengths covering and surrounding from both sides said main absorption peak and a second substance substantially blocking radiation at wavelengths covering said main absorption peak.

13. The method of claim 7, wherein said three sensors include two units of said reference sensor and a single unit of said signal sensor.

14. The method of claim 7, wherein said three sensors include two units of said signal sensor and a single unit of said reference sensor.

15. The method of claim 7, wherein said three sensors include two signal sensors, one of said signal sensors further includes a third optical filter passing wavelengths covering a second main absorption peak of the vapour, yet substantially blocking wavelengths surrounding from both sides said second main absorption peak of the vapour.

16. The method of claim 7, wherein said comparison is accompanied by a re-zeroing procedure in which zero ratios of signals obtained from said signal and reference sensors are redefined in accordance with non-vapour spectral disturbances.

17. A system for increasing the sensitivity of detecting the presence of a predetermined first vapour of a predetermined threshold concentration having a first main absorption peak in a gas in a monitored area in optional presence of a second vapour having a second, yet close, main absorption peak, the system comprising:

(a) a radiation source for providing radiation at wavelengths at least covering and surrounding from both sides said main absorption peaks of the vapours; and (b) three independent sensors including:
(i) a signal sensor including a first radiation sensing element and a first optical filter passing wavelengths covering said first main absorption peak, yet substantially blocking wavelengths from both sides of said first main absorption peak and wavelengths covering said second main absorption peak;
(ii) a reference sensor including a second radiation sensing element and a second optical filter passing wavelengths surrounding from both sides said first main absorption peak, yet substantially blocking wavelengths covering said first and second main absorption peaks; and
(iii) an additional sensor being identical to said signal sensor or to said reference sensor;

wherein an open path exists between said radiation source and each of said sensors such that simultaneously sensing said radiation after passing via said open path through the gas by said three independent sensors and comparing signals obtained from said sensors enables determining a presence or absence of the first vapour of the predetermined concentration in the gas.

18. The system of claim 17, wherein said radiation is effected via a radiation source selected from the group consisting of a flashlamp and a modulated filament lamp.

19. The system of claim 18, wherein said flashlamp is a quarts Xenon flashlamp.

20. The system of claim 17, wherein said second filter is a notch filter.

21. The system of claim 20, wherein said notch filter includes a first substance passing radiation at wavelengths covering and surrounding from both sides said first main absorption peak and a second substance substantially blocking radiation at wavelengths covering said first main absorption peak.

22. The system of claim 17, wherein said first filter includes a first substance passing radiation at wavelengths covering said first main absorption peak and a second substance substantially blocking radiation at wavelengths covering said second main absorption peak.

23. A system for detecting the presence of a predetermined vapour of a gas in a predetermined threshold concentration in a monitored area, the system comprising:

(a) a radiation source for providing radiation at wavelengths at least covering and surrounding from both sides a main absorption peak of the vapour; and (b) three independent sensors including:
(i) a signal sensor including a first radiation sensing element and a first optical filter passing wavelengths covering said main absorption peak, yet substantially blocking wavelengths from both sides of said main absorption peak of the vapour;
(ii) a reference sensor including a second radiation sensing element and a second optical filter passing wavelengths being close from at least one side to said main absorption peak, yet substantially blocking wavelengths covering said main absorption peak of the vapour; and
(iii) an additional sensor being identical to said signal sensor or to said reference sensor;

wherein an open path exists between each of said three independent sensors and said radiation source, such that simultaneously sensing said radiation after passing via said open path through the gas by said three independent sensors and comparing signals obtained from said sensors enables determining a presence or absence of the vapour of the predetermined concentration in the gas, and obviates the need for a beamsplitter.

24. The system of claim 23, wherein said radiation is effected via a radiation source selected from the group consisting of a flashlamp and a modulated filament lamp.

25. The system of claim 24, wherein said flashlamp is a quarts Xenon flashlamp.

26. The system of claim 23, wherein said second filter passes wavelengths surrounding from both sides said main absorption peak, yet substantially blocking wavelengths covering said main absorption peak of the vapour.

27. The system of claim 26, wherein said second filter is a notch filter.

28. The system of claim 37, wherein said notch filter includes a first substance passing radiation at wavelengths covering and surrounding from both sides said main absorption peak and a second substance substantially blocking radiation at wavelengths covering said main absorption peak.

29. The system of claim 23, wherein said three sensors include two units of said reference sensor and a single unit of said signal sensor.

30. The system of claim 23, wherein said three sensors include two units of said signal sensor and a single unit of said reference sensor.

31. The system of claim 23, wherein said three sensors include two signal sensors, one of said signal sensors further includes a third optical filter passing wavelengths covering a second main absorption peak of the vapour, yet substantially blocking wavelengths from both sides of said second main absorption peak of the vapour.

32. The system of claim 23, further comprising a window being substantially transparent to said radiation and positioned in front of said reference sensor.

33. The system of claim 23, further comprising a housing formed with windows being substantially transparent to said radiation and positioned in front of each of said three sensors, said widows being covered with a water repellent material.

* * * * *